United States Patent [19]
Strausak et al.

[11] Patent Number: 5,370,635
[45] Date of Patent: Dec. 6, 1994

[54] DEVICE FOR DELIVERING A MEDICAMENT

[75] Inventors: Sabina Strausak, Basel; Hans Leuenberger, Pfeffingen, both of Switzerland

[73] Assignee: Asulab S.A., Bienne, Switzerland

[21] Appl. No.: 122,492

[22] Filed: Sep. 30, 1993

[30] Foreign Application Priority Data

Feb. 4, 1992 [CH] Switzerland ............... 00309/92

[51] Int. Cl.$^5$ ..................... A61M 5/00; A61K 9/22
[52] U.S. Cl. ..................... 604/248; 604/892.1
[58] Field of Search ............... 604/20, 236, 237, 246, 604/248, 249, 256, 289, 290, 304, 306, 307, 308, 892.1, 131, 890.1; 607/900

[56] References Cited

U.S. PATENT DOCUMENTS

| | | | |
|---|---|---|---|
| 4,474,575 | 10/1984 | Eckenhoff et al. | 604/892.1 |
| 4,533,348 | 8/1985 | Wolfe et al. | 604/246 |
| 4,601,707 | 7/1986 | Albisser et al. | 604/131 |
| 4,619,652 | 10/1986 | Eckenhoff et al. | 604/892.1 |
| 4,783,413 | 11/1988 | Suter | 604/892.1 |
| 4,865,845 | 9/1989 | Eckenhoff et al. | 604/892.1 |
| 4,871,352 | 10/1989 | Tran | 604/892.1 |

FOREIGN PATENT DOCUMENTS

| | | |
|---|---|---|
| 0336543 | 10/1989 | European Pat. Off. |
| 2562800 | 10/1985 | France |
| 2092183 | 7/1980 | Germany |
| 9103271 | 3/1991 | WIPO |

*Primary Examiner*—C. Fred Rosenbaum
*Assistant Examiner*—Frank Wilkens
*Attorney, Agent, or Firm*—Griffin Butler Whisenhunt & Kurtossy

[57] ABSTRACT

A device for delivering a medicament has a membrane (7) with at least one permeable area (7b) permeable to the medicament and a reservoir space (25) which contains a solvent and the medicament at least partially dissolved therein, An adjustable and/or deformable control element (7) is disposed on the side of the membrane (7) facing the reservoir space (25) with which the access of the medicament from the reservoir space (25) to at least one permeable area (7b) of the membrane (7) can be changed. In addition an electronic device (37) is provided with which the control element (17) can be automatically controlled via a motor (37). The device permits the periodic alteration of the delivery rate of the medicament which is advantageous in many cases.

20 Claims, 5 Drawing Sheets

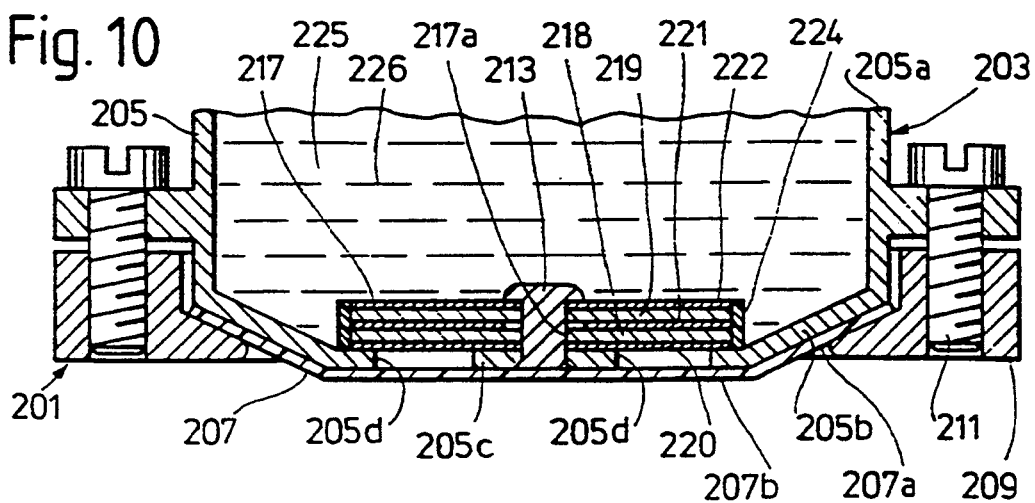
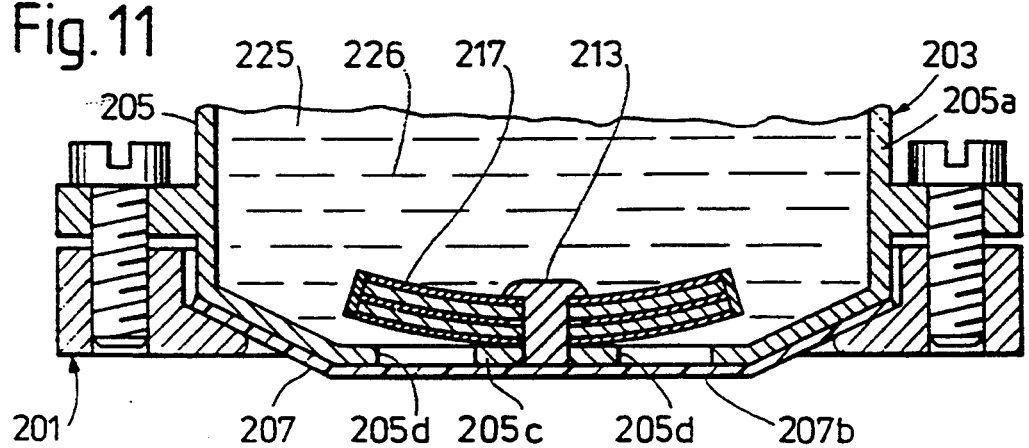

DEVICE FOR DELIVERING A MEDICAMENT

FIELD OF THE INVENTION

The invention relates to a device for delivering a medicament.

The device is intended, in particular, to deliver a medicament and dispense it to an organism for a relatively long period of time, for example at least a few days. The device can, for example, be adapted for positioning on the surface of the skin of a human or possibly an animal body in order to apply a medicament thereto from the outer side thereof. The device may, however, also be implanted in the body of a human or animal in order, for example, to deliver a medicament to the fluid present in a tissue and/or in a cavity of the body.

DESCRIPTION OF THE PRIOR ART

Known devices for delivering a medicament have a reservoir with a reservoir space which contains a solution with the medicament dissolved therein. The reservoir space is at least partially limited by a membrane through which the medicament can diffuse. Devices of this kind can be adapted for the transdermal application of the medicament or for implantation into the body of a human or animal.

Devices of this kind deliver the medicament to or into the organism to be treated during continuous and uninterrupted use until the reservoir is empty. In so doing, the delivery of the medicament occurs at a rate which frequently either decreases continually or is approximately constant for a large part of the delivery process and then, for example, decreases during the final phase of the delivery process. Continuous delivery of this kind is, however, unfavourable in many medicaments for various reasons. For example in the case of various medicaments the need for them and/or their uptake and processing in an organism can vary periodically with time, for example as a result of exogenous influences. In addition, during longer term, constant application of a medicament, such as for example nitroglycerin, an organism can develop so called tolerance—i.e. signs of habituation—which reduce the efficacy of the medicament, with the result that it is either necessary to allow for a decrease in the therapeutic effect, or that the application rate of the medicament has to be increased in the course of the treatment.

Devices are also known for applying a medicament transdermally to an organism by means of iontophoresis. Devices of this type have an electrical battery, an electronic appliance and electrodes. This makes it possible to create an electrical field that produces an electric current containing ions of the medicament which penetrates the body of the organism so that the medicament reaches the body to be treated as a stream of ions. The stream of ions can be applied continuously or intermittently, as desired.

Iontophoresis does, however, have the disadvantage that it is only applicable for medicaments which consist of ions or which can form these. Moreover, the ions have to remain stable under the influence of the electrical field required. In addition, there is a danger in the case of iontophoresis that the electrical field created and the electrically produced current may cause disagreeable tingling, irritation and heating or even burns and/or possibly other damage to the organism.

Other known medicament delivery devices have a reservoir as well as an electrically driven pump. Whereas devices of this type, as required, permit a continuous as well as constant or an intermittent delivery of a medicament, they are, however, only used for implantation into a body and not for the transdermal application of a medicament. Known devices having a pump would also be totally unsuitable for transdermal application of a medicament since they only have a small outlet opening for the medicament, with the result that this would not be likely to be distributed over a sufficiently large area of skin surface for transdermal application. Moreover, it is not possible to make the feed rates of pumps currently available sufficiently small with the result that it is generally necessary to pump the medicament or—to be more accurate—the active substance thereof, into the organism to be treated in greatly diluted form. This has, inter alia, the disadvantage that correspondingly large reservoirs are needed. In addition, an electrically driven pump constantly needs electrical energy during operation, with the result that devices having a pump have to be equipped with a relatively large battery.

DESCRIPTION OF THE INVENTION

It is an object of the invention to provide a device for the delivery of a medicament which makes it possible to avoid the disadvantages of known devices. In so doing, it is in particular intended, starting from known devices with a reservoir and with a membrane permeable to the reservoir medicament, to control the delivery of the medicament in the desired periodic manner and for example periodically to block this or at least to reduce this and then to release or increase this again.

A device for delivering a medicament having a free-flowing solvent and a reservoir space containing medicament at least in part dissolved in said solvent, which has at least one membrane with at least one permeable area permeable to the medicament, characterised by an adjustable and/or deformable control element disposed on the side of the membrane facing the reservoir space to change the entry of the medicament from the reservoir space to at least one permeable area of the membrane. Particularly advantageous embodiments of the invention are set out in the dependent claims.

The medicament stored in the reservoir space of the device to be delivered, i.e. to be dispensed and applied to an organism during use of the device, is dissolved at least in part in a free-flowing, namely flowing or possibly gel-like solvent also present in the reservoir space. The medicament can for example consist of nitroglycerin, oestradiol, scopolamine, nicotine, salbutamol, an analgesic such as indomethacin, an antirheumatic or another active substance. The solvent may, for example, be hydrophobic and consist of a biocompatible, natural and/or synthetic oil—such as castor oil or miglyol. The solvent may, however, also be hydrophobic or consist of a mixture with at least one hydrophobic and at least one hydrophilic component.

The reservoir space of the device thus contains before its use a reservoir and/or filling material which consists at least in part of a solution. The medicament can for example be totally dissolved in the solvent before the delivery procedure and at the commencement thereof. The reservoir and/or filling material may, however, still contain undissolved medicament in addition to the dissolved material before the delivery of the medicament and on commencement thereof. This undissolved portion of the stored medicament may, for example, be present in the form of a plurality of small, solid particles and/or possible drops of liquid which are dispersed in the solvent—i.e. suspended or emulsified—and more or less evenly distributed. The originally undissolved portion of the medicament can, however, also be stored in the form of a compact layer which, for example, adheres to the inner surface of a wall serving to limit the reservoir space. There is also a possibility to divide the reservoir space by a perforated partition wall or the like into two areas, one of which serves as a compartment for accommodating the originally undissolved, solid, for example granular medicament portion, whereas the other reservoir space area then exclusively contains the medicament in a dissolved state. If the reservoir space also contains undissolved medicament in addition to the dissolved medicament, it is of course possible—relative to the volume of the reservoir space—to store a larger amount of medicament than if the reservoir space exclusively contains dissolved medicament.

According to the invention, the membrane has at least one permeable area which is permeable to the medicament to be delivered by the device. The medicament can accordingly diffuse through at least the one permeable area of the membrane. The membrane and the solvent are preferably adjusted to one another and to the type of the medicament in such a way that the membrane is substantially impermeable to the solvent. In this case the membrane should either permit the passage of no solvent at all, or at most so little that, in the case of a medicament delivery procedure, a large portion of the solvent remains in the reservoir area until the intended amount of medicament is delivered. During this process preferably at least 50% by weight of the solvent and more appropriately at least 75% by weight and, particularly preferred, at least 90% by weight of the solvent should remain in the reservoir area until at least 50% by weight and for example at least 75% by weight or, particularly preferred, at least 90% by weight of the initially stored amount of the medicament is delivered.

The membrane should consist of a material resistant to the medicament and to the solvent and should itself not harm the medicament. If the device is intended for the transdermal application of the medicament, the membrane should also be well tolerated by the skin of the human or animal to be treated and thus cause neither irritation nor damage the skin. If the device is intended for implantation into a body of a human or animal, the membrane—as well, incidentally, as all other parts forming outer limiting surfaces of the device—should be biocompatible and have no toxic effects. The membrane may, for example, consist of a foil or a film of a hydrophobic or hydrophilic, porous membrane material—for example plastic. The pores present in the membrane material preferably have an effective size of less than 1 micrometer, the latter corresponding to the mesh size of a sieve and setting down the maximum size of particles allowed to pass therethrough. Porous flexible foils or films composed of polypropylene suitable for the formation of membranes are for example obtainable under the trade marks and designations CELGARD 2400 and CELGARD 2500 from Hoechst Celanese Corporation, Charlotte, N.C. 28217, USA. These foils or films are about 0.025 mm thick and have pores with an effective size of about 0.05 or 0.075 micrometers.

The membrane is preferably connected with the other parts of the device in such a manner that at least one section containing its permeable area or its permeable areas is planar and free of creases and that the outer surface of the cited section of the membrane forms a, for example, planar section of a fictive enveloping surface which surrounds the device, moulds at least partially against the device and exclusively consists of planar and/or convexly bent sections. The device is preferably disposed for use in such a manner on or in the body of the patient or animal to be provided with the medicament that the or each permeable area of the membrane is located under the reservoir space and/or at the lowest point thereof during permanent or at least frequently adopted positions of the patient or animal.

The present, adjustable and/or ductile control element of the device according to the invention makes it possible to change the access of the medicament from the reservoir area to at least one permeable area of the membrane. The control element can exert a function corresponding to the blocking element and/or throttle element of a valve and/or tap.

The control element may for example consist of an adjustable sliding member—such as a rotary sliding member or possible a sliding member displaceable along a straight line. The sliding member can have at least one permeable area having at least one permeable hole and for example several permeable holes or even very many as well as very small permeable holes consisting of through pores. The control element may, however, possibly also be piezoelectrically ductile.

The control element may for example as desired be brought selectively into a release state or a blocked state. The release state is understood to mean that position and/or shape of the control element at which the medicament has the greatest possible access to at least one permeable area of the membrane. The blocked state is understood to mean that position and/or shape of the control element at which the access of the medicament is blocked or at least throttled to the smallest possible value. Here it is proposed to consider in greater detail the case in which the control element does not totally block and only throttles the access of the medicament to the membrane in the blocked state. In this case, the delivery rate of the medicament in the blocked state should be a maximum of 40% and, particularly preferred, a maximum of 30% of the delivery rate of the same concentration of the dissolved medicament in the release state. If the control element is for example brought alternately during certain release time intervals into the release state and during certain blocked time intervals into the blocked state, and if the concentration of the dissolved medicament in such successive time intervals changes, it is possible to approximately represent the values of the delivery rate resulting during at least two successive release time intervals by a release approximation curve or release approximation line which extends at least over one blocked time interval. In addition, the values of the delivery rate resulting in the blocked state can be shown approximately in analogous manner by a blocked approximation curve or blocked approximation line. The approximate value shown at specific point in time by the blocked approximation curve or approximation line should then preferably be a maximum of 40% and, particularly preferred, a maximum of 30% of the value shown at the appropriate point in time by the release approximation curve or approximation line.

It is also possible to provide for the possibility whereby the control element is brought into an intermediate state or alternatively into one of several different intermediate states. In an intermediate state of this kind, the delivery rate of the medicament can then have a value that lies between the values resulting in the release state and in the blocked state.

If the reservoir space only contains dissolved medicament during the delivery of medicaments, the medicament concentration present in the solution first decreases in the vicinity of the membrane and then also in areas further removed therefrom. A concentration gradient therefore develops in the solution. If the control element is brought from the blocked state into the release state and then remains therein for a specific period of time the medicament delivery rate consequently first increases sharply and then falls again. If the control element is then returned to the blocked state and the delivery is thereby interrupted or at least greatly reduced, the concentration gradient in the solution also decreases again with the result that the concentration of the dissolved medicament once again becomes more or less homogenous. If the control element in the blocked state does not totally throttle access of the medicament to the membrane, the medicament concentration in the solution can also decrease during the blocked state.

If the reservoir space contains both dissolved and also undissolved medicament and the control element is brought from the blocked state into the release state, the medicament concentration also falls at least in an area of the solution adjacent to the membrane. However, previously undissolved medicament is dissolved during the delivery process. After a certain period of time, an approximately stationary state can be achieved in which the medicament delivery rate remains approximately constant until the control element is once again brought into the blocked state.

If the reservoir space contains undissolved medicament, the medicament delivery rate therefore changes less in the control element in the release state than if the reservoir space exclusively contains dissolved medicament. In addition, the delivery rates then have maximum values of approximately equal size in different release time intervals, which is advantageous for many applications.

The adjustable and/or ductile control element is preferably disposed as close as possible to the membrane and arranged in such a way and so dimensioned that, in its blocked state, not more than a very small amount of the total amount of solution present in the device is in contact with the permeable area or the permeable areas of the membrane. This results in the time course of the delivery rate also following the changes in the state of the control element relatively rapidly in particular if this is brought from the release state into the blocked state.

The reservoir space of the device is preferably sealed off on all sides by a thick wall and the control element and/or the membrane sealed off against the surroundings of the device. In addition, the reservoir space is preferably completely filled before the device is used by the reservoir and/or filling material consisting at least in part of a solution. If the medicament concentration of the solution present in the reservoir space decreases when the medicament is given, the volume of the solution may also decrease in the course of time under certain circumstances. If the reservoir and/or filling material present in the reservoir space also contains undissolved medicament before use of the device in addition to the dissolved medicament and if this goes into solution during use and is then delivered, the volume of the reservoir and/or filling material decreases approximately by the volume originally occupied by undissolved medicament.

The device can therefore still be equipped with compensation means to compensate volume changes in the reservoir and/or filling material. These compensation means can for example have a deformable compensation element secured to one wall of the reservoir or at least partially adjacent the reservoir space or completely disposed therein which can change its volume in such a manner that it expands with decreasing volume of the reservoir and/or filling material and fills the released volume. The compensation element can for example have a foam rubber body containing closed pores which is compressed before use of the device by the reservoir and/or filling material and expands as the volume of the reservoir and/or filling material decreases. Instead of this, the compensation element can also be formed by a bag or balloon which has a flexible for example resiliently extendable, envelope and a hollow space surrounded on all sides thereby which is for example filled by gas consisting of air, the pressure of which is greater than the air pressure prevailing in the vicinity of the device. Another possibility consists in forming part of the limitation of the reservoir space from a flexible foil, which is pressed against the inside of the reservoir space by a pressure element at least disposed on its outer side and composed of a spring or a foam rubber body. It is also possible to make part of the limitation of the reservoir space of a resilient, stretchable envelope or bellows. The envelope or the bellows can then be pretensioned—i.e. stretched—before the device is used in such a way that it tries to contract when the medicament is delivered.

Since the reservoir space is completely filled with reservoir and/or filling material before the device is used and because any reduction in the volume of the reservoir and/or filling material occurring during delivery of the medicament is compensated by compensation means, it is possible to ensure that the solution comes into contact with the membrane when the control element is in the release state independently of the position of the device.

The control element is preferably electrically controllable, i.e. connected to, or provided with electrically controllable positioning means. These positioning means can for example have an electric motor or at least a piezoelectric element and electrodes. In particular if one admits that the control element in the blocked state does not totally block delivery of the medication, but only throttles it in the manner already described, the device can be devised in such a way that the adjustment and/or deformation of the control element consumes only little energy. This results, inter alia, in the advantage that the energy needed to adjust and/or deform the control element can be supplied by a battery having a relatively small capacity.

In an advantageous embodiment of the device, this electronic, electrically conducting switching means associated with the positioning means can be automatically controlled and for example brought alternately from the blocked state to the release state and back into the blocked state. In so doing it is for example possible to provide that the electronic switching means bring the control element periodically once or several times per period in the release state for a release time period lasting for example from 30 minutes to several hours. If the control element is brought several times into the release state for the duration of a period, it is also possible to provide that the various release conditions have different time intervals from one another and/or last for different lengths of time. The period duration can, for example, last several hours or a whole day or even several days or weeks.

The device can in addition have at least one manually operable operating organ which, if required, gives a patient or nurse the possibility to adjust the period duration and/or the release time period and/or to control the control element manually instead of automatically.

The control element of the device thus makes it possible to deliver the medicament intermittently or at least to alternately markedly reduce and then increase the delivery rate. In so doing, the delivery of the medicament can be effectively adjusted to the type of the medicament and to needs of a patient or animal to which the medicament is dispensed that vary at different times. In addition, the development of tolerance can be prevented or at least greatly reduced. For these reasons it is also possible to reduce the overall amount of medicament to be administered. This, in turn, has the advantage that undesired side effects can be reduced or even totally avoided.

The nitroglycerine cited as a possible medicament can for example be administered transdermally in a daily cycle to a patient suffering from Angina pectoris. In so doing, the control element can be automatically brought temporarily into the release state once or several times daily during normal treatment. If the patient notices, for example, when the control element is in the blocked state that an attack is coming on, he can bring the control element into the release state by bringing the operating organ preferably provided into the release state. It may be possible to also arrange that the control element is only brought into an intermediate state during normal, automatically controlled operation instead of into the release state and that the control element can only be brought into the release state by manual operation of the operating organ.

Oestradiol, also cited as a possible medicament, is a hormone also produced by the female body itself, its natural production rate changing within the menstrual cycle and possibly in addition in the daily rhythm. In a device serving to deliver oestradiol, the control element can for example be controlled in such a way that the oestradiol is given off in a periodically changing manner with a period duration corresponding to a mean menstruation period duration. For this purpose, the control element can for example remain permanently in the blocked state during each period for several days in succession—for about 5 to 10 days—and be brought into the release state in the remaining portion of the period once or several times daily for a release time period that remains constant or varies in the course of one period duration. If oestradiol is delivered at least twice daily, the delivery or release time duration can be set to be the same or different for the various deliveries made on the same day.

In a device designed for the transdermal application of a medicament this can, in a preferred embodiment, have two bands, one end of each of which is secured to a support and/or housing belonging to the device. The other end sections of the bands can then be provided with closure means—for example looped and burred closure means—by means of which the two bands can be detachably connected with one another. Bands of this type make it possible to secure the device for example detachably to the arm or leg of a person or animal. This mode of securing has the advantage that it requires no adhesives which could under certain circumstances cause allergies or other skin irritation.

It is, however, also possible to secure a device intended for the transdermal application of a medicament using at least one adhesive band. The device can then not only be secured to an arm or a leg, but also to the thorax or to any other part of the body. In addition, the device can possibly be completely covered by the adhesive bands and closed in a watertight manner against the environment so that the patient wearing the device can also wash those parts of his body surface surrounding it without difficulty or can even bath and shower

BRIEF DESCRIPTION OF THE DRAWINGS

The object of the invention will now be explained in greater detail according to the embodiments shown in the drawings. The drawings show In FIG. 1 a diagrammatic section of a device for the delivery of a medicament with a rotatable control element shown in the blocked position.

PREFERRED EMBODIMENTS OF THE INVENTION

Figure 1:
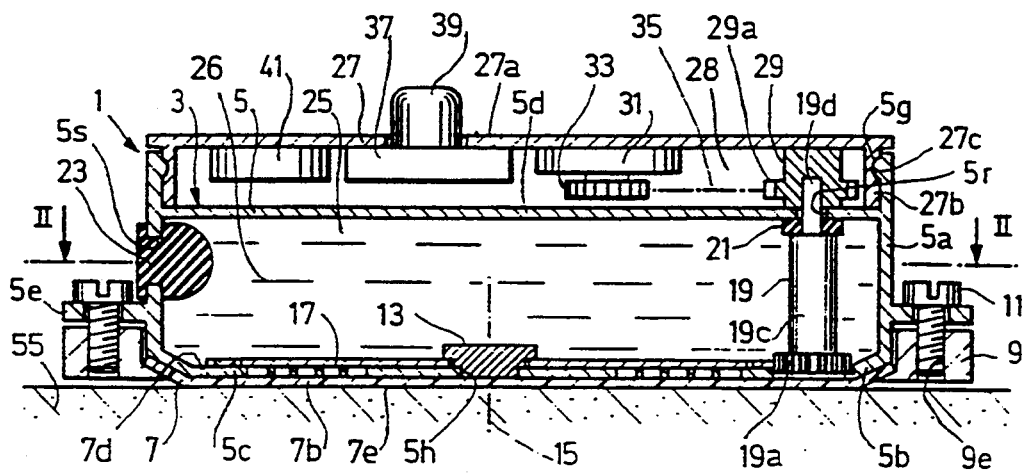
Figure 2:
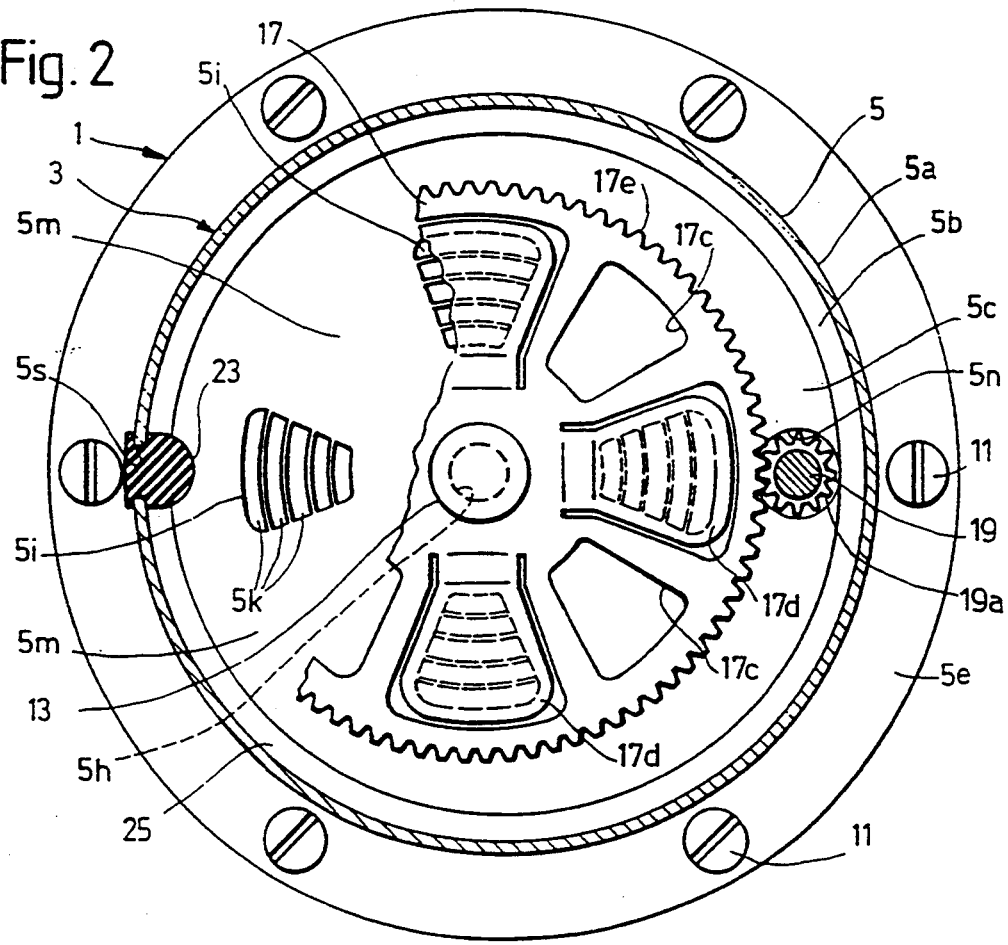
In FIG. 2 a section through the device taken along the line II—II of FIG. 1 wherein one part of the control element is cut away, In FIG. 3 a section from FIG. 1 in larger scale, wherein the gear wheel meshing with the toothing of the control element is also cut away, In FIG. 4 a different section from FIG. 1 of the control element shown in the blocked state to the same scale as FIG. 3, In FIG. 5 a section of the device corresponding to FIG. 4, but with the control element in the release state, In FIG. 6 a diagrammatic cross section through a part of a human body and a view of the device secured to the part of the body in smaller scale than in FIGS. 1 to 5, In FIG. 7 a diagram with a measuring curve showing the time course of medicament delivery of the device, In FIG. 8 a diagrammatic section approximately corresponding to FIG. 3 of another device with a rotatable control element, In FIG. 9 a section through the device partly shown in FIG. 8 along line IX—IX of FIG. 8 in smaller scale than the latter, In FIG. 10 a diagrammatic section of still another device with a piezoelectrically deformable control element shown in the blocked position and In FIG. 11 a section of the device shown in FIG. 10 but with the control element in the release position.
Figure 3:
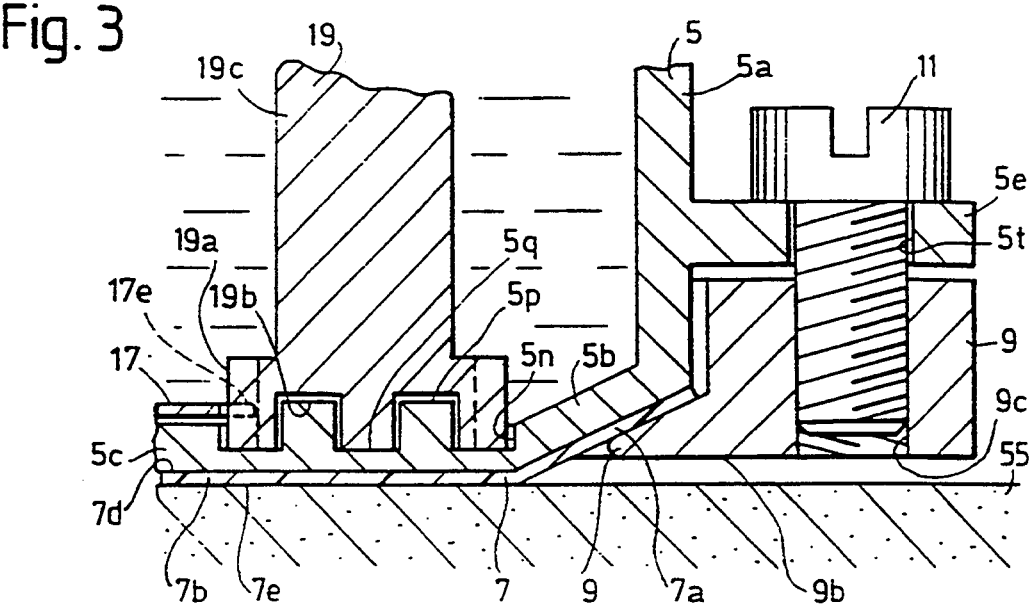
Figure 5:
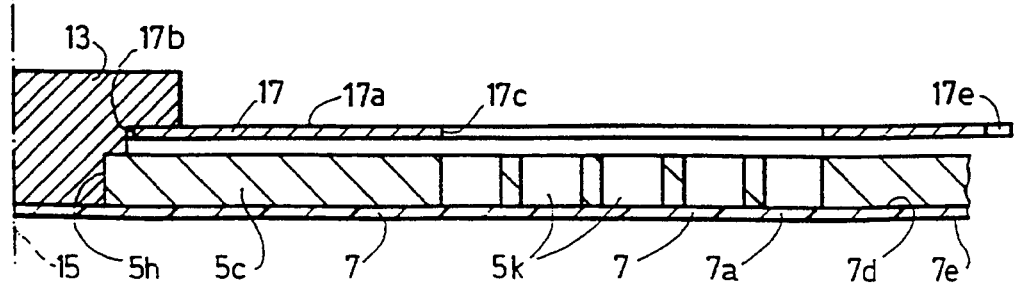
Figure 6:
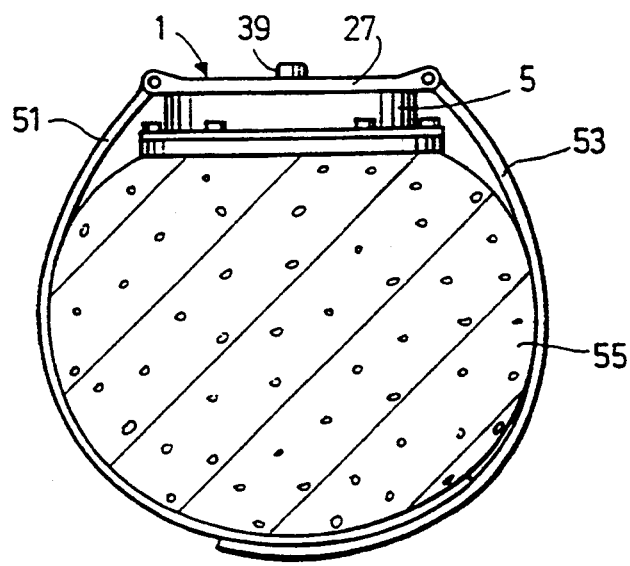

FIGS. 1, 2 and 6 show a entire device for the delivery of a medicament designated with the numeral 1. The device 1 has a reservoir 3 with a reservoir housing 5 also shown in part in FIGS. 3, 4 and 5. This is substantially rotationally symmetrical to an axis (not shown) and has a substantially rigid wall with a cylindrical jacket 5a. This is associated with a first planar radial wall 5c at its end shown at the bottom of FIG. 1 via a conical wall section 5b sloping downwards to the axis of the reservoir container which forms the floor of the reservoir housing 5 in the position of the device shown in FIG. 1. The jacket 5a is associated in the proximity of its other end located at the top of FIG. 1 with a second planar, radial wall 5d serving as a cover. The reservoir housing 5 also has a flange 5e projecting radially outwards away from the jacket 5a. The section of the jacket 5a projecting upwards in FIG. 1 beyond the second wall 5d is provided with at least one inwardly projecting locking projection 5g —namely with a containing rib or with a few cams distributed along the circumference of the jacket. The reservoir housing having the above described parts is drawn diagrammatically in FIG. 1 as a monopart body, but does in fact consist of at least two originally separate and then undetachably or detachably associated parts.

Figure 4:
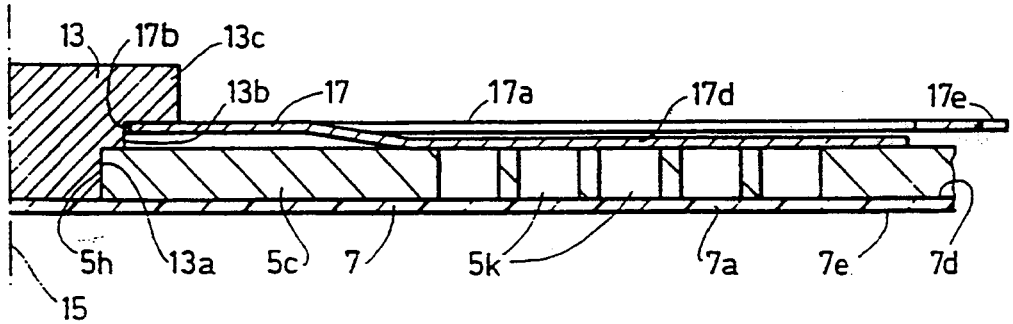

The first wall 5c is provided with a slightly eccentrically disposed hole 5h shown particularly clearly in FIGS. 4 and 5. The first wall 5c also has at least one permeable area 5i, preferably at least two and in fact four approximately permeable areas 5i which are evenly distributed around the hole 5h, have the shape of the sector of a circle and are particularly clearly visible in FIG. 2. The wall 5c is provided at every permeable area 5i with at least one hole 5k penetrating the first wall 5c and namely with five slit-shaped holes 5k. These are separated from one another by narrow ridges and run, as does the latter, along arcs of a circle about the centre of the hole 5h. Between each pair of successive permeable areas 5i following each other along a circle surrounding the hole 5h is a compact—i.e. hole-free—blocking area 5m. The blocking areas 5m extend over a larger central angle than the permeable areas 5i. The inner, upper surface of the planar wall 5c is provided in the proximity of its circumferential position furthest removed from the hole 5h with an annular recess 5n —i.e. ring groove—particularly clearly visible in FIG. 3, which surrounds a peg 5p. This projects slightly beyond the inner, upper surface of the remaining part of the first wall 5c and is provided in the centre with a blind hole 5q.

The second planar wall 5d has a through hole 5r, the centre of which is in alignment with a direction parallel to the axis of the reservoir housing with the centre of the recess 5n and of the blind hole 5q. The jacket 5a is provided with a hole 5s. In addition, the flange 5e has holes 5t distributed about its circumference.

A porous flexible membrane 7, porous to the medicament to be dispensed, is secured to the exterior of the reservoir housing 5 has an edge area 7a adjoining the outer conical surface of the conical wall section 5b and a planar permeable area 7b which adjoins the outer, lower surface of the first planar wall 5c. The inner surface of the membrane permeable area 7b adjoining this is designated 7d. The outer surface of the membrane permeable area is designated 7e. The conical outer surface of the wall section 5b and the edge area 7a of the membrane 7 are preferably inclined by a maximum or 45° and, more particularly preferred, by a maximum of 30° against the first planar wall 5c, with the result that the membrane 7 and in particular its permeable area 7b remains smooth and uncreased.

A clamping ring 9 used to secure the membrane 7 has a section surrounding the jacket 5b below the flange 5e and a projection 9a projecting inwards therefrom which clamps the edge area 7a of the membrane 7 to the conical wall section 5b. As shown particularly clearly in FIG. 3, the lower, radial and planar limiting surface 9b of the clamping ring 9 is located above the outer surface 7e of the planar permeable area 7b of the membrane 7. In the position of the device 1 shown in FIGS. 1 and 3 to 5, the planar membrane outer surface 7e forms the lowest-lying section of an enveloping surface of the device formed of planar and convexly bent sections. The clamping ring is provided with threaded borings 9c and is secured to the reservoir housing by screws 11 which penetrate the holes 5t and are screwed into the threaded borings 9c.

A bearing 13 particularly clearly shown in FIGS. 4 and 5 has a peg 13a fixed therein and at least relatively securely sitting in the hole 5h, for example by pressing and/or riveting, an enlargement 13b with a shoulder surface adjoining the inner upper surface of the first wall 5c and a head 13c located at a small distance from the first wall 5c. The bearing 13 defines an eccentric axis 15 parallel to the axis of the reservoir housing 5.

A control element 17 consists of a substantially circular washer and has a planar main section 17a. This is provided in the centre with a circular hole 17b, the edge of which surrounds the enlargement 13b of the bearing 13 as is particularly clearly visible in FIGS. 4 and 5. The control element 17 is radially and axially supported by the bearing 13 so that it can be rotated about the axis 15 or tilted to and fro. The control element 17 has at least one permeable hole 17c as well as at least one blocking area 17b whereby in each case four permeable holes 17c and blocking areas 17d are provided distributed about the axis 15. The permeable holes 17c have approximately or exactly the same shape in a projection parallel to the axis 15 as the contour shape of the permeable areas 5i defined in part by edges of the holes 5k. Each blocking area 17d of the control element 17 consists of a sprung tongue which, together with the remaining parts of the control element, is formed from a monopart body. The end of the tongue closest to the axis 15 forms the root thereof and is connected with the planar main section 17a of the control element limiting the hole 17a and the permeable holes 17c. The free edges of each tongue are separated from the remaining control element by a slit running therealong. Each tongue has by its root a section inclined outwards and downwards—i.e. towards the first planar wall 5c —away from the main section 17a, and, for example, bent at right angles as shown in FIG. 4. The sections of the tongues set against the first wall 5c can adjoin the inner surface of the first planar wall 5c in a sprung manner. The main section 17a of the control element 17 supported with a small axial play by the bearing 13 is lifted so far from the wall 5c by the spring effect of the tongues until it impinges against the radial surface of the head 13c facing the first wall 5c. The control element 17 is provided with toothing 17e along its circumference.

When the control element 17 is in the blocked state or in the blocked position according to FIGS. 1, 2 and 4, the section of each blocking area 17d of the control element 17 set against the first wall 5c and thereadjoining covers a permeable area 5i of the first wall 5c. As shown in FIG. 2, each blocking area 17d formed by a tongue projects into a projection parallel to the axis 15 on all sides slightly above the holes 5k belonging to the appropriate permeable area 5i in such a way that this more or less tightly closes these holes 5k.

When the control element 17 is rotated about the axis 15 at an angle of 45° it reaches its release state or its release position. As shown in FIG. 5, each permeable hole 17c of the control element 17 is then located above the holes 5k of one of the permeable areas 5i of the first wall 5c. In the release state of the control element 17 each permeable hole 17c is thus at least partially and for example totally as well as exactly overlapping the corresponding permeable area 5i.

The control element 17 thus forms a rotary valve. A transfer element 19 serving to turn the control element has a toothed wheel 19a meshing with the toothing 17b of the control element 17. The diameter thereof and its number of teeth are substantially smaller than the diameter and number of teeth of the control element 27. The toothed wheel 19a has a recess 19b, namely a circular groove visible in FIG. 3, on the front at the bottom of FIGS. 1 and 3. The toothed rim of the toothed wheel 19a surrounding this projects in axial direction into the annular recess 5n of the first wall 5c. The annular, hollow cylindrical peg 5p thereof correspondingly projects into the recess 19b of the toothed wheel 19a in such a way that this is radially supported and axially borne by the first wall 5c. The transfer element 19 has a shaft 19c firmly associated with the toothed wheel 19a, for example consisting together therewith of a monopart body. This projects through the hole 5r of the second planar wall 5d and is supported there. The shaft 19c is provided above the second wall 5d with a coupling section 19d, the purpose of which will be explained below. The passage of the shaft 19c through the second wall 5d is sealed by a seal 21.

The reservoir housing 5, the clamping ring 9, the control element 17 and the drive element 19 consist for example of a metallic material, such as stainless steel or titanium. The membrane 7 consists for example of one of the foils cited in the introduction obtainable under the designation CELGARD 2400 or CELGARD 2500. It should also be noted that FIGS. 1 to 6 are in part not drawn to scale in the interest of improved clarity. The membrane 7 and in part also the control element 17 have in particular been drawn with exaggerated thickness. The outer diameter of the jacket 5a can for example be about 3 cm to 4 cm . The first planar wall 5c can for example be about 0.5 mm thick. The membrane 7 can have a thickness of about 0.5 mm. The membrane 7 can have a thickness of 0,025 mm. The material thickness of the control element 17 can for example be 0.07 mm to 0.2 mm. The axial play of the control element between the membrane 7 and the head of the bearing 13 is for example at most or about, 0.01 mm.

The hole 5s is tightly closed by a closure element 23. This serves as a septum, consists of a resilient material and is so disposed that the hole 5s and the closure element 23 can be perforated by a hollow needle and the closure element 23 tightly seals the hole 5c after withdrawal of the needle. The free area of the inner space of the reservoir 3, i.e. that part not occupied by the bearing 13, control element 17, drive element 19 and closure element 23, forms the reservoir space 25 thereof. This is filled before the device is used with a reservoir and/or filling material 26 which consists, according to the introduction, at least in part of a solution. The closure element 23 can possibly also serve as a compensation element in order to compensate volume changes of the reservoir and/or filling material 26 in the manner described in the introduction.

A support 27 has a for example planar, disc-shaped cover part 27a and a projecting ring portion 27b located in FIG. 1 axially downwards therefrom in the section of the jacket 5a located above the second wall 5d of the reservoir housing 5. The outer surface thereof has at least one locking recess 27c, namely a ring groove or indentations distributed along the circumference of the ring portion. The at least one locking projection 5g of the reservoir housing 5 and the at least one locking recess 27c of the support 27 together form locking and connecting means which firmly but detachably associate the support 27 of the manufactured, ready-for-use device with the reservoir housing 5. The support 27 also serves as part of a housing formed thereby together with the reservoir housing 5.

An only diagrammatically drawn coupling element 29 with bearing means (not shown) is rotatably supported in the inner space between the wall 5d of the reservoir housing 5 and the cover part 27a of the support 27. Together with the coupling section 19d of the transmission element 19 this forms a detachable coupling so that the coupling element 29 is torsionally coupled with the transmission element 19 on binding the support 27 with the reservoir housing 5 and is uncoupled again from the transmission element on removing the support 27 from the reservoir housing 5. The coupling section 19d and the coupling element 29 have carrier means engaging in each other for example in the coupled state. The coupling element 29 has, for example, a hole into which the coupling section 19d can be inserted when the support 27 is bound with the reservoir housing 5. The circumferential surface of the coupling section 19d and the limiting surface of the hole provided in the coupling element 29 can then, for example, have flattened parts which form the carrier means. Instead of these, there may also be carrier means with at least one projection or peg engaging detachably in a hole or in a groove. The coupling element 29 is, for example, also provided with or firmly associated with a toothed wheel 29a.

An electric motor 31 is also disposed in the inner space 28 and secured to the support 27. The motor 31 is, for example, designed as a stepping motor of the type used for wristwatches. A toothed wheel 33 located on the shaft of the motor 31 and rotatable thereby is associated by a gear box 35 diagrammatically indicated by a dash-dotted line with the toothed wheel 29a, but could instead be directly engaged therewith. The electrically drivable and controllable motor 31 forms positioning means for adjusting the control element 17 together with the toothed wheel 33, the gear box 35, the coupling element 29 and the transmission element 19.

The motor 31 is associated in an electrically conducting manner with an electronic device 37 secured to the support 27. This has electronic switching means for controlling the motor 31—i.e. switching it on and off. The electronic switching means can for example have a programmable integrated circuit. The electronic device 37 is provided and/or electrically associated with at least one operating organ 39. This is manually operable from the vicinity of the device and can for example be formed by a switching device with a push button which projects through a hole provided in the cover part 27a. The operating organ 39 or one of the operating organs can, however, possibly also have a manually tiltable or rotatable button. A battery 41 disposed like the electronic device 37 in the inner space 28 and secured to the support 27 is electrically conducting with the electronic device 41 and associated therethrough and/or directly with the motor 31.

The reservoir space 25 of the device is filled before its use with the reservoir and/or filling material 26 containing the medicament to be stored. The membrane 7 can be tightly closed before or after filling of the reservoir space 25 by an adhesive and removable foil or by other detachable closing means until the device is used. If the reservoir and/or filling material 26 consists of a pure solution or of a solution containing fine, dispersed particles or droplets, the reservoir space 25 can be evacuated during and/or after manufacture of the reservoir 3. The entire reservoir and/or filling material can then be placed into the reservoir space 25 using a hollow needle temporarily inserted through the closure element 23.

On the other hand, if the reservoir and/or filling material has a solid portion in the form of large grains or a solid layer adhering to the inner surface of the reservoir housing or another solid and relatively large body, this solid portion of the reservoir and/or filling material may possible already be added to the reservoir space 25 before this is closed by binding of originally separate parts of the reservoir housing and/or insertion of the closure element 23 against the environment. After closing the reservoir space this can then be filled with a solution or with a solvent used to form such a solution which is inserted with a hollow needle through the closure element 23.

Two of the bands 51, 53 shown in FIG. 6 are secured by their ends to the support 27. The other end sections of the two bands 51, 53 are provided with looped and burred closure means or the like so that they can be detachably connected with one another.

The electronic device 37 can be formed during manufacture of the device 1 and programmed to automatically control the motor 31 during use of the device for periodic medicament delivery. It is also possible to provide for the period duration of the delivery cycles and/or the release time duration and/or another process parameter to be individually adjusted before use of the device. This can, for example, occur by actuating at least one operating organ 39 or with the aid of at least one positioning organ which is located in the inner space 28 and becomes accessible by separating the support 27 from the reservoir housing 5.

To use the device 1, the optionally sealing foil or the otherwise present closure means are removed and the device is detachably secured using the bands 51, 53 to a part of the body 55 of a man or animal consisting for example of an arm. The device 1 then lies firmly with the outer surface 7e of the membrane 7 on the skin surface of the part of the body 55. The device can then be put into operation by operating the or one operating organ 39 so that the electronic device 37 controls the motor 31 in the prescribed manner.

When the device is used, the motor 31 can tilt or rotate the control element 17 about the transmission element 19. In so doing, the control element 17 can be periodically tilted about a central angle of 45° and thus brought alternately into the blocked state and the release state. The control element may possibly also be brought in an intermediate state or into an intermediate position in which the tongues serving as blocking areas 17d only partially cover and close the holes 5k of the permeable areas 5i.

During use of the device this gives off medicament previously diluted in the reservoir and/or filling material 26 and presents this transdermally to the part of the body 55. The solvent then remains in the reservoir space 25. When the supply of medicament is more or less completely used up or application of the medicament is no longer required, the device 1 can be removed from the body part 55. In addition, the support 27 together with the parts 29, 31, 33, 35, 37, 39, 41 held thereby can be separated from the reservoir and connected to another reservoir, the reservoir space of which contains medicament, for the next use. The previously used reservoir can be thrown away or possibly completely emptied, cleaned, sterilised and filled so as to be used again.

To study the delivery of a medicament an experimental device devised similarly to device 1 was affixed to a measuring device instead of to a body part. This made it possible to collect medicament diffusing through the membrane in a cell containing water, and the amount of medicament collected was determined from time to time. The control of the control element conducted in such an experiment and the resultant delivery rate are set out in the diagram in FIG. 7. In this trial, the reservoir space contained as medicament salicylic acid which was entirely dissolved in an oil. The volume of solution stored was 2.5 $cm^3$. The time t in minutes is shown on the abscissa shown at the bottom of FIG. 7. On the ordinate of the lower partial diagram located directly above the abscissa, the state of the control element designated with S is shown, the value 0 corresponding to the blocked state and the value 1 to the release state. In the upper part of the diagram the delivery rate Q is shown on the ordinate. To determine Q the amount of salicylic acid passing out of the reservoir space and diffusing through the membrane was determined at 15-minute intervals.

The rectangular control curve 61 drawn in the lower partial diagram shows the time course of the state of the control element 17 selected for the trial. This was brought at the beginning of the measurement at time $t_o$ =0 to the release state, left therein for 30 min, brought at time $t_1$ into the blocked state, left therein for 150 min, returned to the release state again at time $t_2$, left therein for 120 min and returned to the blocked state again at time $t_3$. The measured curve 63 in the upper partial diagram shows the time course of the delivery rate Q measured at this state. It may be seen that the delivery decreases in the course of the release time interval and also during the blocked time interval. A release approximation line 65 is shown in a broken line in the upper partial diagram which compensates the fluctuations of the measured values measured in the two successive release time intervals and that bridges the blocked time interval lying between these time intervals. The approximation line 67, also shown as a broken line, balances in analogous manner the fluctuations of the measured values measured in the two blocked time intervals and bridges the release time interval lying between these time intervals. A comparison between approximation values belonging to the same points in time shown by the two approximation lines 65 and 67 shows that the delivery rates balanced and approximated in the cited manner in the blocked state are about 15 to 20% of the delivery rates occurring in the release state. Experiments were also conducted in which the reservoir space still contained undiluted salicylic acid and the concentration of the dissolved salicylic acid remained constant during delivery. In these trials, the delivery rates in the blocked state also remained about 15 to 20% of the delivery rates occurring in the release state.

Figure 8:
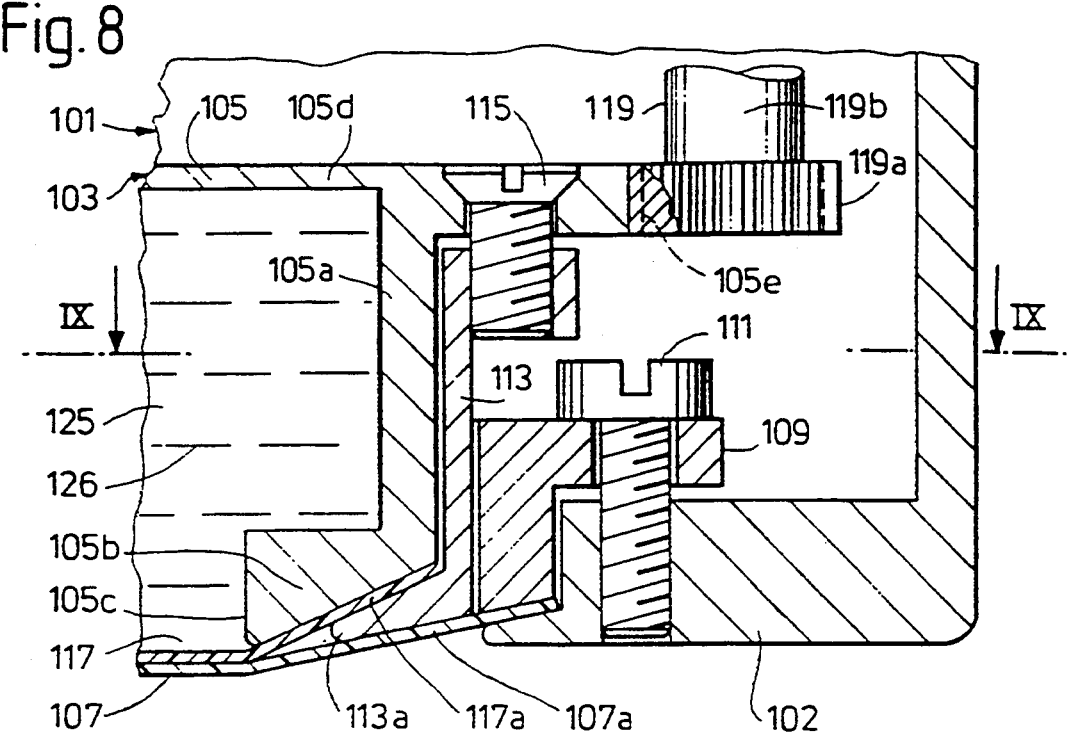
Figure 9:
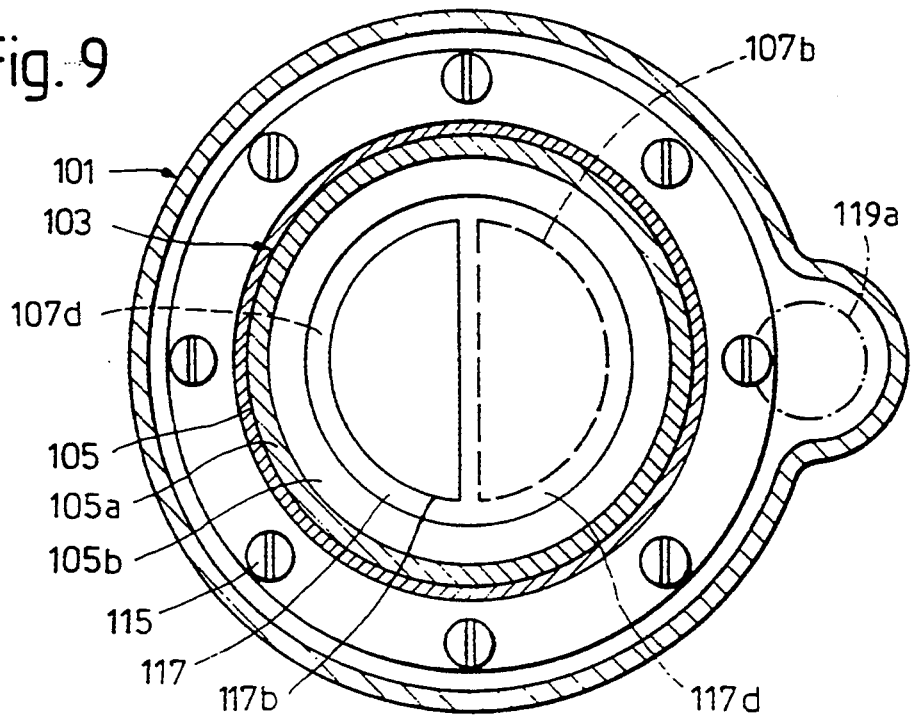

The device partially shown in FIG. 8 and also in FIG. 9 and designated as a whole with the numeral 101 has a fixed outer housing 102 and a reservoir 103 with a reservoir housing 105 that is rotatable in the housing 102 about the common axis of the two housings. The reservoir housing 105 has a cylindrical jacket 105a, at the lower end of which there adjoins a wall section 105b with a conical outer surface. Instead of the first planar wall 5c, the reservoir container 105 has an opening 105c limited by the inner edge of the wall section 105b and is thus open at the lower end. The reservoir container 105 has at the upper end of the jacket 105a a radial and planar wall 105d corresponding to the second wall 5d of the reservoir container 5 and also a toothing 105e passing about its axis.

A membrane 107 abuts with its edge area 107a against a conical area section of the outer housing 102 and is detachably secured to the outer housing 102 with securing means having an outer clamping ring 109 as well as screws 111.

An inner clamping ring 113 has a jacket disposed between the jacket 105a of the reservoir housing 105 and the outer clamping ring 109 and a projection 113a projecting therefrom towards the inside between the reservoir housing-wall section 105b and the membrane edge section 107a. The inner clamping ring 113 is retained with screws 115 to the reservoir housing 105 and together with these constitutes securing means for the detachable securing of a control element 117 to the reservoir housing 105. The control element 117 is formed by a flexible foil and has an edge section 117a which abuts against the conical outer surface of the wall section 105b of the reservoir housing 105 and is firmly clamped by the projection 113a of the inner clamping ring 113 to the wall section 105b.

The membrane 107 and the control element 117 are, for example, composed of foils which consist of one of the porous membrane materials mentioned in the introduction. The membrane 107 and the foil constituting the control element 117 is, however, only permeable to the medicament in an approximately semicircular permeable area 107b or 117b. The remaining areas of the membrane 107 and the control element 117 or at least of the planar, circular sections of the membrane and the control element located in axial projection within the opening 105c, are impermeable to the medicament and constitute a blocking area 107d or 117d respectively. During the manufacture of the device 101, the pores of the foils originally permeable to the medicament throughout can be closed and/or covered in the blocking areas to be formed. This can for example occur by applying a closure material—possibly by steaming on metal or spraying on of a varnish. It is, however, also possible to stick thin, pore-free foils to the porous foils as closure material.

In the position of the device 101 shown in FIG. 8, the outer surface of the planar, circular section of the membrane 107 forms the lowest-lying outer surface thereof. The reservoir housing 105 and the control element 117 secured thereon are preferably supported radially and axially in such a way by the outer clamping ring 109, the membrane 107 and additional support means (not shown), that the control element 117 abuts against the membrane 107 in all possible positions of the device 101 and in particular of the outer housing 102 thereof, but can easily slide thereover. A rotatable transmission element 119 has a toothed wheel 119a meshing with the toothing 105e of the reservoir housing 105 as well as a shaft 119b firmly associated therewith. Together with the control element 117, the reservoir housing 105 limits the reservoir space 125 in which the reservoir and/or filling material 126 is stored.

In the position of the reservoir housing 105 shown in FIGS. 8 and 9 and of the control element 117 secured thereon, the latter is in its blocking state and covers the permeable area 107b of the membrane 107 with its blocking area 117d in such a way that hardly any medicament reaches the permeable area 107b. When the reservoir housing 105 is rotated together with the control element 117 secured thereto about a central angle of 180°, the latter passes into the release state in which the two permeable areas 107b and 117b cover each other. The medicament contained in the reservoir and/or filling material 126 can then diffuse through the two permeable areas.

The shaft 119a of the transmission element 119 is radially and axially supported with support means of a support (not shown) which is detachably associated with the outer housing 102 as well as with the reservoir housing 105. In common with the support 27 of the device 1, the support of the device 101 (not shown) contains an electric motor, an electronic device and a battery.

Trials were also conducted with an experimental set-up designed substantially similarly to the device 101. In these trials, the delivery rate in the blocked state was less than 10%, namely about or at most 5% of the delivery rate resulting in the release state. In the case of device 101, the ratio between the delivery rates resulting in the blocked state and in the release state is thus smaller and therefore more favourable than in the case of the device 1. Nevertheless, the device 101 needs a greater torque and more energy to rotate the control element than needed by device 1. Otherwise, the device 101 can be used in similar manner to the device 1.

The device 201 shown in part in FIGS. 10 and 11 has a reservoir 203 with a reservoir housing 205. This has a jacket 205a, a wall section 205b with a conical outer surface and a planar wall 205c associated therewith. This has at least one through hole 205d and a few holes 205d disposed about its centre. A membrane 207 is secured by its edge area 207a to the wall section 205b with the aid of a clamping ring 209 and of screws 211 and abuts with its permeable area 207b against the planar wall 205c. A control element 217 with the shape of a circular disc has a hole 217a in its centre and is secured, for example riveted, in the centre of the planar wall 205c with a securing element 213 penetrating the hole.

The control element 217 consists of a multi-layer sandwich body and has at least one disc-shaped piezoelectric element and, in particular, two such elements 218, 219. The control element 217 also has three laminated electrodes 220, 221, 222. The lowest electrode 220 and the uppermost electrode 222 are electrically conductive with one another and associated with the earth connection of an electronic device (not shown). The middle electrode 221 is separated from the securing element 213 by an annular gap, electrically insulated to the outside at the outer edge by an insulation 224 and associated in electrically conducting manner by an isolated conductor with one control connection of the electronic device. The reservoir space 225 contains a reservoir and/or filling material 226.

When no electric voltage is applied to the electrodes of the control element 217, the control element is in its blocked state shown in FIG. 10, in which has the shape of a planar disc and closes the holes 205d . The electronic device can now apply an electrical direct voltage to the electrodes, it being possible for example to apply to the middle electrode 221 a positive voltage compared to the two other electrodes 220, 222. The two piezoelectric elements 218, 219 can be disposed and polarised in such a way that the electrical voltage applied causes a radial expansion of the lower element 218 and a radial contraction of the upper element 219. This distorts the control element 217 according to FIG. 11 by bending it away from the wall 205c in the area of the holes 205d so that it passes into its release state.

The devices may also be changed in other ways. The housing 5, 102, 105, 205, and the clamping rings 9, 109, 113, 209 can for example be made of plastic instead of a metallic material, such as of the polymethylene oxide obtainable under the trade name DELRIN from Du Pont de Nemours. The wall thicknesses of the housing can then, if necessary, be somewhat larger compared to their diameters than shown in the various figures. If the housing and clamping ring consist of a thermoplastic plastic, the rings can be associated together using an ultrasonic-welded bond instead of by screws. The thickness of the rings measured in an axial direction can then perhaps be made smaller compared to their diameter than in the case of the clamping rings 9, 109, 209. In addition, it may also be possible to make smaller the angle formed by the edge area lying between one housing and one ring of one membrane with their planar main section, without the ring projecting over the membrane in axial direction. The membranes can then be firmly clamped as in the devices described with reference to the various figures between the housings and the clamping rings. The membranes may, however, also be welded and/or bonded with the housings and rings. Under certain circumstances it may even be possible to secure the membranes without rings by welding and/r gluing to the housings. This may make it possible to secure the membranes without kinking or bending their edge areas in such a way that the membranes can be completely planar.

It may also be possible to manufacture the control element 17 of plastic instead of a metallic material. In addition, the blocking areas 17d of the control element 17 may possibly form a monopart disc by means of sections connected everywhere with the remaining control element 17 and lying in one surface planar therewith.

In addition, the toothings 17e, 105e formed in toothed rims closed per se, may possibly be replaced by toothings which only partly surround the tilt axis of the corresponding control element. It may even be possible to omit the toothing 17e of the control element 17 as well as the transmission element 19 and instead to associate the control element firmly with a shaft coaxial to the axis 15. This can then be associated through an uncoupled coupling disposed above the wall 5d with a gear box retained by the support 27 through a tight through-bearing provided in the centre of the second planar wall 5d. The support 27 can be associated with the reservoir housing by screws instead of by locking means. If the above mentioned shaft replacing the transmission element 19 is disposed coaxially to the jacket of the reservoir housing, it is also possible to provide the reservoir housing jacket and the support with threads which can be screwed together. The closure element 27 forming a septum can, moreover, be disposed in the second planar wall 5d of the reservoir housing instead of in the jacket. In addition, the control element 107 can be provided with two or more permeable areas and the same number of blocking areas distributed about its axis.

Figure 7:
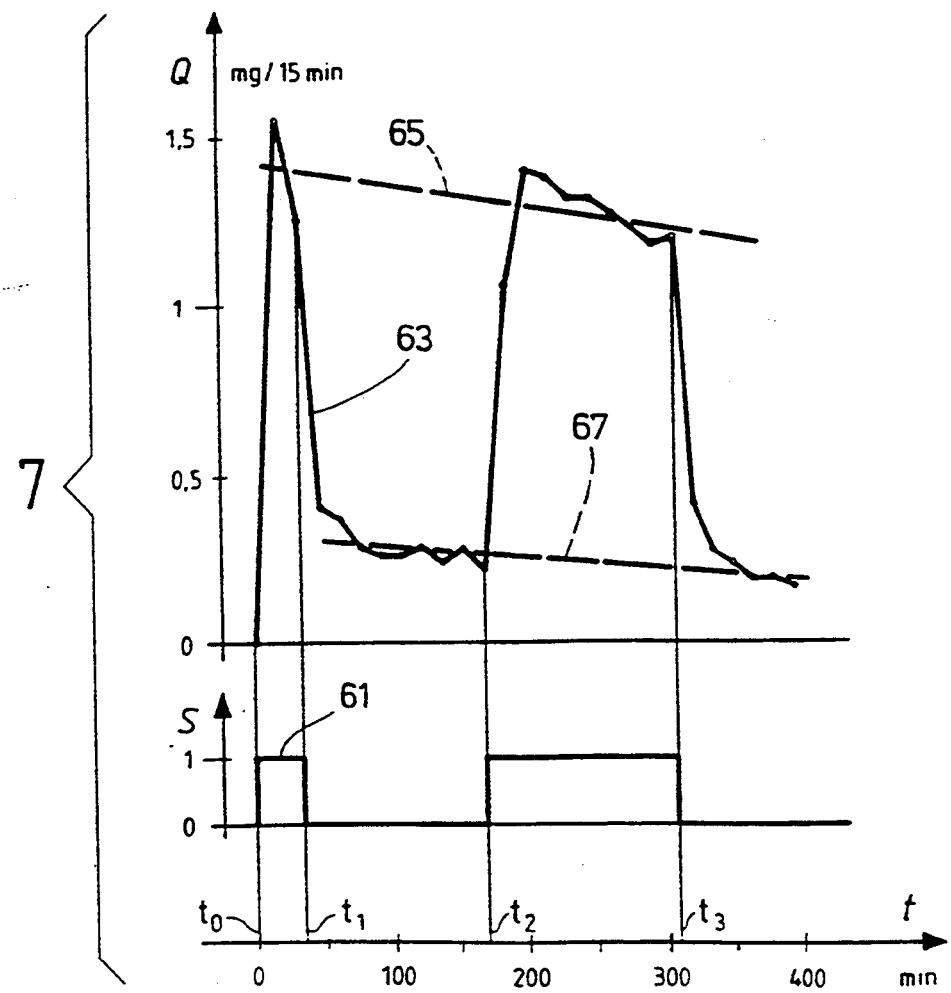

The rotatable control element 17 of the devices 1 and 101 respectively can—as described for the control element 17 with reference to FIG. 7—be tilted intermittently and stepwise and thus alternately brought into the release state and into the blocked state. It may also be possible to provide for a rotatable control element to rotate evenly during the entire period of use of the device. The time course of medicament delivery can then for example be set in general according to the device constituting device 1 by the numbers, arrangements and dimensions of the permeable areas 5i and the permeable holes 17c and by the angular velocity of the control element 17. It is, for example, possible to provide only a single permeable area 5i in the wall 5c and only a single permeable hole 17 or several permeable holes 17c in the rotatable control element 17. The or each permeable hole 17c can thereby extend approximately over an central angle or arc of equal size about the axis 15 as in the case of the permeable area 5i. Instead, it is also possible to provide that the or each permeable hole 17 extends over a substantially larger or over a substantially smaller central angle than the permeable area 5i, with the result that an approximately constant medicament delivery rate is periodically achieved despite the continuous rotation of the control element with constant angular velocity during a specific time. If several permeable holes 17c are available, these can have the same dimensions and be evenly distributed. It is, however, also possible to arrange that the permeable holes 17c extend over different central angles and/or are irregularly distributed about the axis 15. In such a case, medicament is delivered for time intervals of two more or less differing lengths and/or irregularly distributed with a rotation of the control element about an angle of 360½ occurring with a constant angular velocity. Instead of a single permeable area 5i and several permeable holes 17c it is, of course, also possible to provide several permeable areas 5i and only one single permeable hole 17c. In addition, it is also possible to provide several permeable areas 5i as well as several permeable holes 17c, where the number of permeable holes 17c may possibly be different to the number of permeable areas 5i. In device 101, the numbers, dimensions and distributions of the permeable areas 107b and 117b may be changed in analogous manner.

In device 201, the wall 205c may perhaps be provided with a resiliently deformable seal surrounding all holes 205d.

We claim:

1. A device for delivering a medicament in a free-flowing solvent, said device comprising:
   a reservoir housing bounding a reservoir space containing said medicament at least in part dissolved in said solvent;
   at least one membrane with at least one permeable area permeable to the medicament; and,
   an adjustable control element disposed on a side of said membrane facing said reservoir space for controlling movement of said medicament from said reservoir space to said at least one permeable area.

2. A device as claimed in claim 1 wherein said control element comprises a sliding member adjustable parallel to a section of said membrane having said at least one permeable area.

3. A device as claimed in claim 1 wherein said permeable area of said membrane has an inner surface abutting against a planar wall area of said reservoir housing, said planar wall area having at least one through hole, said device further including means mounting said control element for rotation about an axis whereby said control element may be moved into a blocked state or a release state where it respectively covers or uncovers said at least one through hole.

4. A device as claimed in claim 3 wherein said planar wall has at least two permeable areas about said axis with each permeable area having at least one through hole, and said control element has a permeable hole and a blocking area for each permeable area of said planar wall, said permeable holes and said blocking areas of said control element being distributed about said axis whereby each blocking area of said control element covers one permeable area of said planar wall when said control element is in said blocked state and each permeable hole of said control element at least partially overlaps said planar wall with one permeable area when said control element is in its release state.

5. A device as claimed in claim 4 wherein said control element has a planar main section limiting each permeable hole, and each blocking area comprises an elastic tongue associated with said main section and having a section disposed resiliently lying against said planar wall.

6. A device as claimed in claim 2 wherein said membrane comprises a foil with pores which are open in each permeable area of said membrane, said membrane has at least one blocking area, impermeable to said medicament, in which said pores are closed, and said control element is mounted for rotation about an axis and has at least one permeable area with open pores permeable to said medicament and at least one impermeable blocking area impermeable to the medicament, said control element being rotatable about said axis between a closed state and a release state, each said permeable area of said membrane being covered by one of said blocking areas of said control element when said control element is in said closed state and covered by one permeable area of the control element when the control element is in the release state.

7. A device as claimed in claim 1 and further comprising an electric motor for adjusting said control element.

8. A device as claimed in claim 1 and further comprising at least one piezoelectric element for deforming said control element.

9. A device as claimed in claim 1 and further comprising electronically controllable adjusting means for adjusting said control element and an electronic device for automatically controlling said control element to periodically change the rate of movement of said medicament from said reservoir space to said at least one permeable area.

10. A device as claimed in claim 9 and further comprising a battery, a motor for adjusting said control element and a support detachably attached to said reservoir housing for holding said motor, said battery and said electronic device, said battery, said motor and said electronic device being removable from said reservoir housing with said support.

11. A device as claimed in claim 2 wherein said permeable area of said membrane has an inner surface abutting against a planar wall area of said reservoir housing, said planar wall area having at least one through hole, said device further including means mounting said control element for rotation about an axis whereby said control element may be moved into a blocked state or a release state where it respectively covers or uncovers said at least one through hole.

12. A device as claimed in claim 11 wherein said planar wall has at least two permeable areas about said axis with each permeable area having at least one through hole, and said control element has a permeable hole and a blocking area for each permeable area of said planar wall, said permeable holes and said blocking areas of said control element being distributed about said axis whereby each blocking area of said control element covers one permeable area of said planar wall when said control element is in said blocked state and each permeable hole of said control element at least partially overlaps said planar wall with one permeable area when said control element is in its release state.

13. A device as claimed in claim 12 wherein said control element has a planar main section limiting each permeable hole, and each blocking area comprises an elastic tongue associated with said main section and having a section disposed resiliently lying against said planar wall.

14. A device as claimed in claim 6 and further comprising an electric motor for adjusting said control element.

15. A device as claimed in claim 8 and further comprising electronically controllable adjusting means for adjusting said control element and an electronic device for automatically controlling said control element to periodically change the rate of movement of said medicament from said reservoir space to said at least one permeable area.

16. A device as claimed in claim 15 and further comprising a battery, a motor for adjusting said control element and a support detachably attached to said reservoir housing for holding said motor, said battery and said electronic device, said battery, said motor and said electronic device being removable from said reservoir housing with said support.

17. A device as claimed in claim 3 and further comprising electronically controllable adjusting means for adjusting said control element and an electronic device for automatically controlling said control element to periodically change the rate of movement of said medicament from said reservoir space to said at least one permeable area.

18. A device as claimed in claim 14 and further comprising electronically controllable adjusting means for adjusting said control element and an electronic device for automatically controlling said control element to periodically change the rate of movement of said medicament from said reservoir space to said at least one permeable area.

19. A device as claimed in claim 17 and further comprising a battery, a motor for adjusting said control element and a support detachably attached to said reservoir housing for holding said motor, said battery and said electronic device, said battery, said motor and said electronic device being removable from said reservoir housing with said support.

20. A device as claimed in claim 18 and further comprising a battery, a motor for adjusting said control element and a support detachably attached to said reservoir housing for holding said motor, said battery and said electronic device, said battery, said motor and said electronic device being removable from said reservoir housing with said support.

* * * * *

UNITED STATES PATENT AND TRADEMARK OFFICE
CERTIFICATE OF CORRECTION

PATENT NO. : 5,370,635
DATED : December 6, 1994
INVENTOR(S) : Sabina Strausak and Hans Leuenberger It is certified that error appears in the above-indentified patent and that said Letters Patent is hereby corrected as shown below:

Title page, item "[22] Filed: Sep. 30, 1993" should read--
item
--[22] PCT Filed: Feb. 4, 1993 item [86] PCT No.: PCT/CH93/00030

§371 Date: Sep. 30, 1993

§102(e) Date: Sep. 30, 1993 item [87] PCT Pub. No.: WO93/14808

PCT Pub. Date: Aug. 5, 1993 --.

Signed and Sealed this

Twenty-fourth Day of January, 1995

Attest:

BRUCE LEHMAN

Attesting Officer

Commissioner of Patents and Trademarks